US009801838B2

(12) United States Patent
Santhosh et al.

(10) Patent No.: US 9,801,838 B2
(45) Date of Patent: *Oct. 31, 2017

(54) PROCESSES FOR THE PREPARATION OF 2,5-DIHYDROXYBENZENESULFONIC ACID SALTS

(71) Applicant: AmDerma Pharmaceuticals, LLC, Bridgewater, NJ (US)

(72) Inventors: Unni Santhosh, Chennai (IN); Annadurai Marimuthu Senthilkumar, Chennai (IN); Bodireddy Mohan Reddy, Chennai (IN); Rajendran Kamala, Chennai (IN); Mahender Rao Siripragada, Chennai (IN)

(73) Assignee: AMDERMA PHARMACEUTICALS, LLC, Bridgewater, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 14/642,851

(22) Filed: Mar. 10, 2015

(65) Prior Publication Data

US 2015/0183732 A1    Jul. 2, 2015

Related U.S. Application Data

(63) Continuation of application No. 12/811,621, filed as application No. PCT/IB2009/005014 on Jan. 2, 2009, now Pat. No. 9,012,692.

(30) Foreign Application Priority Data

Jan. 3, 2008    (IN) .............................. 21/CHE/2008

(51) Int. Cl.
C07C 309/42    (2006.01)
A61K 31/185    (2006.01)
(Continued)

(52) U.S. Cl.
CPC .......... *A61K 31/185* (2013.01); *C07C 303/06* (2013.01); *C07C 303/22* (2013.01); *C07C 309/42* (2013.01)

(58) Field of Classification Search
None
See application file for complete search history.

(56) References Cited

U.S. PATENT DOCUMENTS 3,509,207 A    4/1970    Esteve-Subirana
3,629,327 A    12/1971    Esteve-Subirana
(Continued)

FOREIGN PATENT DOCUMENTS

GB    1419995          1/1976
WO    WO-2005/013962  2/2005
WO    WO-2008/113863  9/2008

OTHER PUBLICATIONS

Final Office Action in U.S. Appl. No. 12/811,621, dated Sep. 11, 2014, 9 pages.
(Continued)

*Primary Examiner* — Clinton Brooks
(74) *Attorney, Agent, or Firm* — Servilla Whitney LLC

(57) ABSTRACT

Processes for the preparation of 2,5-dihydroxybenzenesulfonic acid salts of formula (I) and a crystalline form of potassium 2,5 2,5-dihydroxybenzenesulfonic acid are provided.

(Continued)

PXRD pattern of potassium 2,5-dihydroxybenzenesulfonic acid (Example 6)

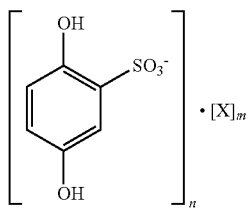

(I)

13 Claims, 2 Drawing Sheets

(51) Int. Cl.
*C07C 303/06* (2006.01)
*C07C 303/22* (2006.01)

(56) References Cited

U.S. PATENT DOCUMENTS

| 4,146,636 | A | 3/1979 | Esteve Soler |
| 5,969,015 | A | 10/1999 | Zinke et al. |
| 6,147,112 | A | 11/2000 | Esteve-Soler |
| 9,012,692 | B2 * | 4/2015 | Santhosh ............... C07C 309/42 568/33 |
| 2007/0149618 | A1 | 6/2007 | Cuevas Sanchez et al. |

OTHER PUBLICATIONS

Final Office Action in U.S. Appl. No. 13,343/374, dated Mar. 24, 2015, 9 pages.
MSDA sheet for 50% Ethanol Solution, 2009, 4 pages.
Non-Final Office Action in U.S. Appl. No. 12/811,621, dated Apr. 9, 2014, 7 pages.
Non-Final Office Action in U.S. Appl. No. 12/811,621, dated Dec. 28, 2012, 5 pages.
Non-Final Office Action in U.S. Appl. No. 13/343,374, dated Sep. 11, 2014, 9 pages.
PCT International Search Report in PCT/IB2009/005014, dated Jul. 7, 2009, 5 pages.
PCT International Preliminary Report on Patentability in PCT/IB2009/005014, dated Jul. 6, 2010, 6 pages.
Gao, Yan, et al., Synthesis of Copoly(aryl ether ether nitrile)s Containing Sulfonic Acid Groups for PEM Application, *Macromolecules*, vol. 38 2005, 3237-3245.
Non-Final Office Action in U.S. Appl. No. 14/948,888 dated Dec. 19, 2016, 13 pages.
Final Office Action in U.S. Appl. No. 14/948,888 dated Aug. 24, 2017, 6 pages.

* cited by examiner

Figure 1: PXRD pattern of potassium 2,5-dihydroxybenzenesulfonic acid (Example 6)

Figure 2: PXRD pattern of potassium 2,5-dihydroxybenzenesulfonic acid (Example 7)

PROCESSES FOR THE PREPARATION OF 2,5-DIHYDROXYBENZENESULFONIC ACID SALTS

CROSS-REFERENCE TO RELATED APPLICATIONS

This application is a continuation of U.S. application Ser. No. 12/811,621, filed Mar. 1, 2011, which is the National Stage entry of PCT/IB2009/005014, filed on Jan. 2, 2009, which claims priority to Indian Patent application number 21/CHE/2008, filed on Jan. 3, 2008, all of which are incorporated herein by reference in their entireties.

The foregoing application, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

The foregoing application, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

TECHNICAL FIELD

Processes for the preparation of 2,5-dihydroxybenzenesulfonic acid salts of the formula (I) are described:

(I)

The compounds of the formula (I), wherein X is at least one cation, and m and n are independently 1 or 2, are known as salts of 2,5-dihydroxybenzenesulfonic acid or hydroquinonesulfonic acid.

BACKGROUND 2,5-Dihydroxybenzenesulfonic acid derivatives and specifically calcium dobesilate, ethamsylate and persilate are known in the art as active agents for the treatment of male sexual dysfunction and other vascular disorders of endothelial origin, both alone and in combination with other agents. U.S. Pat. No. 6,147,112 describes a method for the use of 2,5-dihydroxybenzenesulfonic acid derivatives, preferably calcium dobesilate, ethamsylate and persilate.

Calcium dobesilate or hydroquinone calcium sulfonate, with the chemical name 2,5-dihydroxybenzenesulfonic acid calcium salt, is being sold as Dexium (Delalande) and Doxium (Carrion), and a process for its preparation is described in U.S. Pat. No. 3,509,207.

The potassium salt of 2,5-dihydroxybenzenesulfonic acid, formula (Ia), is also an important compound.

(Ia)

Combinations of active substances comprising a 2,5-dihydroxybenzenesulfonic acid compound including potassium 2,5-dihydroxybenzenesulfonate are disclosed in International Application Publication No. WO2005/013962. Compositions and methods of use for 2,5-dihydroxybenzenesulfonic acid compounds and their pharmaceutically acceptable salts, including potassium 2,5-dihydroxybenzenesulfonate, are discussed in U.S. Patent Publication No. 20070149618.

In view of the importance of the potassium salt of 2,5-dihydroxybenzenesulfonic acid, it is desirable to develop a process for its manufacture by a simple method with improved yield, purity and stability.

SUMMARY

It is an object of the invention to provide a simple, commercially viable, and industrially scalable process for the preparation of compounds of the formula (I), which involves simple isolation of the product and work-up.

Accordingly, the present invention provides a process for the preparation of compounds of formula (I)

(I)

wherein X is at least one cation, and m and n are independently 1 or 2, said process comprising:
  i) sulfonation of hydroquinone of formula (II) in the presence or absence of solvent, to a compound of formula (III);

(II)

(III)

ii) treating the compound of formula (III) with salts of an organic acid in a suitable solvent; and iii) precipitating the product of formula (I).

It is a further object of the invention to provide a process for the removal of inorganics, if formed, in the process of the preparation of compounds of formula (I), which process comprises:

1. dissolving the crude potassium salt of 2,5-dihydroxybenzenesulfonic acid in water;
2. adding a water-miscible solvent to precipitate the inorganics; and
3. isolating the product of formula (I).

In certain embodiments, the invention relates to a process for the preparation of compounds of formula (I)

(I)

wherein X is at least one cation, and m and n are independently 1 or 2, said process comprising: (i) sulfonation of hydroquinone of formula (II) in presence or absence of solvent, to provide a compound of formula (III):

(ii) treating the compound of formula (III) with salts of organic acid in a suitable solvent; and (iii) precipitating the product of formula (I).

In certain embodiments, X is selected from the group consisting of lithium, sodium, potassium, rubidium, cesium, beryllium, magnesium or calcium. In a particular embodiment, X is potassium; m is 1; and n is 1. In some embodiments, the salt of organic acid used is potassium 2-ethylhexanoate. In another embodiment, the salt of organic acid used is potassium 2-ethylhexanoate; X is potassium; m is 1; and n is 1.

In some embodiments, the salt of organic acid used is calcium 2-ethylhexanoate. In certain embodiments, the salt of organic acid used is calcium 2-ethylhexanoate; X is calcium; m is 1; and n is 2.

In another embodiment, X is selected from the group consisting of $[NH_{4-p}R_p]^+$; wherein p at each occurrence is independently selected from an integer from 0 to 4; and each R is independently a $C_1$-$C_4$ alkyl group, a $C_4$-$C_7$ cycloalkyl group, aryl group, or heteroaryl group. In a particular embodiment, X is selected from the group consisting of diethylamine group $[(C_2H_5)_2NH_2]^+$, piperazine and pyridine.

In some embodiments, the sulfonation is carried out using sulfuric acid, fuming sulfuric acid, or a halosufonic acid. In a particular embodiment, the sulfonation is carried out using sulfuric acid.

In some embodiments, the solvent used in (i) is selected from the group consisting of $C_5$-$C_{12}$ alkanes, $C_5$-$C_{12}$ cycloalkanes, and $C_1$-$C_{12}$ haloalkanes; or mixtures thereof. In certain embodiments, the solvent used in (i) is selected from the group consisting of n-heptane, n-hexane, n-octane, dichloromethane and 1,2-dichloroethane.

In some embodiments, the solvent used in (ii) is selected from the group consisting of $C_5$-$C_{12}$ alkanes, $C_5$-$C_{12}$ cycloalkanes, $C_1$-$C_{12}$ haloalkanes, $C_2$-$C_8$ alkyl acetates, $C_2$-$C_{12}$ alkyl ethers, $C_5$-$C_{10}$ cycloalkyl ethers and mixtures thereof. In certain embodiments, the solvent used in (ii) is selected from the group consisting of ethyl acetate, n-heptane, and n-butyl acetate.

In other embodiments, the invention relates to a crystalline form of potassium 2,5-dihydroxybenzenesulfonic acid having characteristic 2θ values of 8.8, 13.7, 15.6, 18.9, 21.4, 26.8, 27.7 and 30.3 (±1).

In some embodiments, the invention relates to a process for the preparation of a compound of formula (I)

(I)

wherein X is potassium, and m and n are each 1, said process comprising: (i) sulfonation of hydroquinone of formula (II) using sulfuric acid to provide a compound of formula (III):

(ii) treating the compound of formula (III) with potassium 2-ethylhexanoate; and (iii) precipitating the product of formula (I).

In yet other embodiments, the invention relates to a process for the removal of inorganics formed in the preparation of compounds of formula (I), which process comprises the steps of: (i) dissolving the crude compound of formula (I) in water; (ii) adding a water-miscible solvent selected from the group consisting of alcohols, ketones, and nitriles to precipitate the inorganics; and (iii) isolating the product of formula (I).

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may be further understood in conjunction with the accompanying drawings, in which.

DETAILED DESCRIPTION

For the purposes of this application, unless otherwise stated in the application, the following terms have the terminology indicated below.

Alkyl refers to both straight and branched carbon chains; references to individual alkyl groups are specific for the straight chain (e.g., butyl=n-butyl). In one embodiment of alkyl, the number of carbon atoms is 1-8, in another embodiment of alkyl, the number of carbon atoms is 1-4 carbon atoms and in yet another embodiment of alkyl, the number of carbon atoms is 1-2 carbon atoms.

Aryl refers to a $C_6$-$C_{14}$ aromatic ring structure. In one embodiment of aryl, the moiety is phenyl, naphthyl, and anthracenyl. In another embodiment of aryl, the moiety is phenyl. The aryl group can be optionally substituted with one or more substituents.

Heteroaryl refers to a $C_5$-$C_{14}$ aromatic ring structure, wherein at least one atom other than carbon is present in the aromatic ring structure. In one embodiment of heteroaryl, the moiety is pyridyl. In another embodiment of heteroaryl, the moiety is pyrimidinyl. Other examples of heteroaryl moieties include, for example, thiophenyl, pyrazinyl, furanyl, imidazolyl, pyrrolyl, pyrazolyl, oxazolyl, isoxazolyl, thiazolyl, quinolinyl, benzothiophenyl, benzimidazolinyl, benzofuranyl, benzisoxazolyl, and the like. The heteroaryl group can be optionally substituted with one or more substituents.

Cyclo as a prefix (e.g., cycloalkyl) refers to a saturated or unsaturated cyclic ring structure having from three to eight carbon atoms in the ring, the scope of which is intended to be separate and distinct from the definition of aryl above. In one embodiment of cyclo, the range of ring sizes is 4-7 carbon atoms; in another embodiment of cyclo the range of ring sizes is 3-4. Other ranges of carbon numbers are also contemplated depending on the location of the cyclo-moiety on the molecule.

Alcohol refers to alkyl and cycloalkyl groups attached to an —OH group, and may include, by way of non-limiting example, isopropyl alcohol, ethyl alcohol, cyclohexyl alcohol and the like.

All stereoisomers (for example, geometric isomers, optical isomers and the like) of the present compounds (including those of the salts and solvates of the compounds), such as those which may exist due to asymmetric carbon atoms on various substituents, including enantiomeric forms, rotameric forms, atropisomers, and diastereomeric forms, are contemplated within the scope of this invention.

When any variable (e.g., aryl, heteroaryl, R, X, m, n, etc.) occurs more than once in any constituent or formula, the definition thereof on each occurrence is independent of its definition at every other occurrence.

This application contemplates all acceptable acid or base salt forms of the compounds, where applicable. The term "acid" contemplates all inorganic or organic acids.

Inorganic acids include mineral acids such as hydrohalic acids, such as hydrobromic and hydrochloric acids, sulfuric acids, phosphoric acids and nitric acids.

Organic acids include all aliphatic, alicyclic and aromatic carboxylic acids, dicarboxylic acids, tricarboxylic acids and fatty acids. Preferred acids are straight chain or branched, saturated or unsaturated $C_1$-$C_{20}$ aliphatic carboxylic acids, which are optionally substituted by halogen or by hydroxyl groups, or $C_6$-$C_{12}$ aromatic carboxylic acids. Examples of such acids are carbonic acid, formic acid, fumaric acid, acetic acid, propionic acid, isopropionic acid, valeric acid, α-hydroxy acids, such as glycolic acid and lactic acid, chloroacetic acid, benzoic acid, methanesulfonic acid, and salicylic acid. Examples of dicarboxylic acids include oxalic acid, malic acid, succinic acid, tataric acid and maleic acid. An example of a tricarboxylic acid is citric acid. Fatty acids include all saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylsteric acid. Other acids include gluconic acid, glycoheptonic acid and lactobionic acid.

The term "base" contemplates all inorganic or organic bases. Such bases include, for example, the alkali metal and alkaline earth metal salts, such as the lithium, sodium, potassium, magnesium or calcium salts. Organic bases include the common hydrocarbyl and heterocyclic amine salts, which include, for example, the diethylamino, morpholine and piperidine salts.

The term "cation" contemplates all organic and inorganic positively charged ions. The cation in the compounds of formula (I) may include, by way of non-limiting example, those described in "Handbook of Pharmaceutical Salts: Properties, Selections and Use", Stahl, H. and Wermuth, C., ed., Verlag Helvetica Chemica Acta, Zurich, Wiley-VCH, 2002.

The term "organic cation" contemplates all positively charged organic ions. Exemplary organic cations include alkyl substituted ammonium cations, cycloalkyl substituted ammonium cations, unsubstituted ammonium cations, primary, secondary and tertiary amines, alkyl amines, cycloalkyl amines, aryl amines, N,N'-dibenzylethylenediamine and the like;

The term "inorganic cation" refers to a positively charged metal ion. Exemplary inorganic cations include Group I and Group II metal cations, such as, for example, lithium, sodium, potassium, rubidium, cesium, beryllium, magnesium, calcium and the like.

Water-miscible organic solvents include, by way of non-limiting example, ketones such as, for example, acetone; alcohols, such as, for example, ethyl alcohol or isopropyl alcohol; and nitriles, such as, for example, acetonitrile. Other water-miscible solvents are apparent to the skilled artisan, and may be further discussed, for example, in "The Chemist's Companion: A Handbook of Practical Data, Techniques, and References," Gordon, A. J. and Ford, R. A., John Wiley and Sons, New York, 1972.

Reagents for sulfonation may be selected from any employed in the art, including, by way of non-limiting example, sulfuric acid, fuming sulfuric acid, and halosulfonic acids (such as fluoro- or chloro-sulfonic acid).

The acids, bases, reagents, additives, temperatures, and solvents used in the invention will be apparent to those of ordinary skill in the art (e.g., *Comprehensive Organic Transformations*, R. C. Larock, VCH Publishers (1989); *Vogel's Textbook of Practical Organic Chemistry* (5$^{th}$ Edition), Furniss et al., Longman Scientific & Technical (1989); *Protective Groups in Organic Synthesis* (3$^{rd}$ Edition), Greene & Wuts, Wiley Interscience (1999); *March's Advanced Organic Chemistry: Reactions, Mechanisms, and Structure* (6$^{th}$ Edition), March & Smith, Wiley, (2007); *Advanced Organic Chemistry (Part A—Structure and Mechanisms—4$^{th}$ Edition)*, Carey & Sundberg, Springer Science (2000); *Advanced Organic Chemistry (Part B—Reaction and Synthesis—4$^{th}$ Edition)*, Carey & Sundberg, Springer Science (2001); *Strategic Applications of Named Reactions in Organic Synthesis*, Kurti and Czako, Academic Press (2005)).

Compounds of the invention may be present in the form of solvates, particularly in the form of hydrates.

It will be appreciated by the skilled artisan that the terminology for compositions and structures referred to herein encompasses those compositions and structures known in the art.

In one embodiment, the present invention provides a process for the preparation of compounds of formula (I), wherein X is potassium, and m and n are each 1, which comprises:
  i) treating the compound of formula (III) with potassium 2-ethylhexanoate in an organic solvent; and
  ii) isolating the product of formula (I).

In another embodiment, the cation is an inorganic cation.

In another embodiment, the cation is an organic cation.

In another embodiment, the cation is an inorganic cation selected from the group consisting of sodium, potassium, lithium, calcium or magnesium.

In another embodiment, the cation is an organic cation selected from the group consisting of $[NH_{4-p}R_p]^+$; wherein p at each occurrence is independently selected from an integer from 0 to 4; and each R is independently a $C_1$-$C_4$ alkyl group, a $C_4$-$C_7$ cycloalkyl group, aryl group, or heteroaryl group.

In another embodiment of the invention, the cation is an organic cation selected from the group consisting of diethylamine groups $[(C_2H_5)_2NH_2]^+$, piperazine or pyridine.

In another embodiment of the invention, the compound of formula (I) is potassium 2,5-dihydroxybenzene sufonic acid (potassium dobesilate).

In another embodiment of the invention, the compound of formula (I) is calcium 2,5-dihydroxybenzene sufonic acid (calcium dobesilate).

In another embodiment of the invention, the compound of formula (I) is magnesium 2,5-dihydroxybenzene sufonic acid (magnesium dobesilate).

In another embodiment of the invention, the compound of formula (I) is diethylamine 2,5-dihydroxybenzene sufonic acid (ethamsylate).

In another embodiment, the present invention provides for the preparation of compounds of formula (I), wherein the solvent used in step i) is selected from $C_5$-$C_{12}$ alkanes, $C_5$-$C_{12}$ cycloalkanes, and $C_1$-$C_{12}$ haloalkanes, or mixtures thereof.

In a preferred embodiment, the solvent used in (i) is selected from alkanes such as, for example, n-hexane, n-heptane, n-octane, cyclohexane; or chlorinated solvents such as dichloromethane and 1,2-dichloroethane.

In a further preferred embodiment, the solvent used in (i) is n-heptane.

In another embodiment, the present invention provides for the preparation of compounds of formula (I), wherein the solvent used in (ii) is selected from $C_5$-$C_{12}$ alkanes, $C_5$-$C_{12}$ cycloalkanes, $C_1$-$C_{12}$ haloalkanes, $C_2$-$C_8$ alkyl acetates, $C_2$-$C_{12}$ alkyl ethers, and $C_5$-$C_{10}$ cyclic alkyl ethers (e.g.—tetrahydrofuran, dioxane, and the like, or mixtures thereof.

In yet another embodiment, the solvent used in (ii) is selected from ethyl acetate, n-heptane, n-butyl acetate and the like or mixtures thereof.

In another embodiment, the invention provides a process for making a crystalline form of potassium 2,5-dihydroxybenzenesulfonic acid having characteristic 2θ values of 8.8, 13.7, 15.6, 18.9, 21.4, 26.8, 27.7 and 30.3 (±1).

In another embodiment, salts of organic acids used in (ii) are selected from group I or II metal salts.

In another embodiment, salts of organic acids used in (ii) are selected from amine salts.

In a further embodiment, organic acids used in (ii) are selected from $C_1$-$C_{10}$ straight chain or branched carbocyclic acids.

In yet another embodiment, salts of organic acids used in (ii) are selected from potassium 2-ethylhexanoate and the like. It is advantageous to employ potassium 2-ethylhexanoate in the precipitation of a compound of formula (I), which in turn results in easy isolation of the formed product. The combination of a potassium salt of an organic acid and suitable reaction solvent renders the formation of a potassium salt to of 2,5-dihydroxybenzenesulfonic acid as a precipitate, thereby avoiding the use of co-solvents, precipitants, or complete evaporation for precipitation of product, making the process industrially viable for scale-up.

In a further embodiment, the water-miscible organic solvent used in (ii) is selected from acetone, alcohols such as, for example, isopropyl alcohol (IPA), and the like or mixtures thereof.

In further embodiments, the process described herein may be conveniently followed for the preparation of salts other than the potassium salt of 2,5-dihydroxybenzenesulfonic acid by using suitable salts of an organic acid source. For example, sodium 2-ethylhexanoate or calcium 2-ethylhexanoate could be used in the preparation of sodium or calcium salts of 2,5-dihydroxybenzenesulfonic acids, respectively.

The use of sodium dithionate in the reaction process yielded the compound of formula (I) with an improved color. Whenever required, the product formed is recrystallized or washed with suitable solvents to have improved quality of the final product with lesser impurities, thereby making it more suitable for pharmaceutical formulation.

The invention will be further described by the following examples, which are provided by way of illustration only and should not be construed to limit the scope of the invention.

Process for the Preparation of Potassium Salt of 2,5-dihydroxybenzenesulfonic Acid

Example 1

Hydroquinone (25 g, 0.2270 mol) n-heptane (75 mL) was taken in a round bottom flask, after cooling the flask to about 10-15° C., sulfuric acid (36 N, 22.2 g) was added dropwise at the same temperature and stirring continued further for about 10-15 min. Temperature was slowly raised to 50-55° C. then stirring continued for 3 h. The reaction mass was then cooled to 25-35° C. and ethyl acetate (250 mL) added to dissolve the solid formed. A solution of potassium 2-ethylhexanoate (41.3 g, 0.2265 mol) in ethyl acetate (250 mL) was added slowly. The reaction was further stirred for an hour. The precipitated crude solid was filtered, washed with ethyl acetate.

Example 2

Hydroquinone (20 g, 0.1816 mol) and n-heptane (60 mL) was taken in a round bottom flask, after cooling the flask to about 10-15° C., sulfuric acid (36 N, 17.8 g) was added dropwise at the same temperature and stirring continued further for about 10-15 min. The temperature was slowly raised to 50-60° C. then stirred for 3-8 h. The reaction mass was then cooled to 25-35° C., n-heptane was decanted and ethyl acetate (200 mL) added to dissolve the solid formed. A solution of potassium 2-ethylhexanoate (36.4 g, 0.1996 mol) in ethyl acetate (200 mL) was added slowly. The reaction was further stirred for an hour. The precipitated crude solid was filtered, washed with ethyl acetate to give 40 g of 2,5-dihydroxybenzenesulfonic acid potassium salt.

Example 3

Hydroquinone (10 g, 0.09 mol) was taken in a round bottom flask, after cooling the flask to about 10-15° C., sulfuric acid (36 N, 8.9 g) was added dropwise at the same temperature and stirring continued further for about 10-15 min. Temperature was slowly raised to 50-60° C. then stirred for 3-8 h. The reaction mass was then cooled to 25-35° C. and ethyl acetate (100 mL) added to dissolve the solid formed. A solution of potassium 2-ethylhexanoate (18.2 g, 0.099 mol) in ethyl acetate (100 mL) was added slowly. The reaction was further stirred for an hour. The precipitated crude solid was filtered, washed with ethyl acetate to give 16 g of 2,5-dihydroxybenzenesulfonic acid potassium salt.

Example 4

Hydroquinone (10 g, 0.09 mol) and dichloromethane (30 mL), was taken in a round bottom flask, after cooling the flask to about 10-15° C., sulfuric acid (36 N, 8.9 g) was added dropwise at the same temperature and stirring continued further for about 10-15 min. Temperature was slowly raised to 30-40° C. then stirred for 1-2 h. The reaction mass was then cooled to 25-35° C. and ethyl acetate (100 mL) added to dissolve the solid formed. A solution of potassium 2-ethylhexanoate (18.2 g, 0.099 mol) in ethyl acetate (100 mL) was added slowly. The reaction was further stirred for an hour. The precipitated crude solid was filtered, washed with ethyl acetate to give 16 g of 2,5-dihydroxybenzenesulfonic acid potassium salt.

Example 5

Hydroquinone (10 g, 0.09 mol) and 1,2-dichloroethane (30 mL) was taken in a round bottom flask, after cooling the flask to about 10-15° C., sulfuric acid (36 N, 8.9 g) was added dropwise at the same temperature and stirring continued further for about 10-15 min. Temperature was slowly raised to 40° C. then stirred for 3-8 h. The reaction mass was then cooled to 25-35° C. and ethyl acetate (100 mL) added to dissolve the solid formed. A solution of potassium 2-ethylhexanoate (18.2 g, 0.099 mol) in ethyl acetate (100 mL) was added slowly. The reaction was further stirred for an hour. The precipitated crude solid was filtered, washed with ethyl acetate to give 18 g of 2,5-dihydroxybenzenesulfonic acid potassium salt.

Example 6

Figure 1:
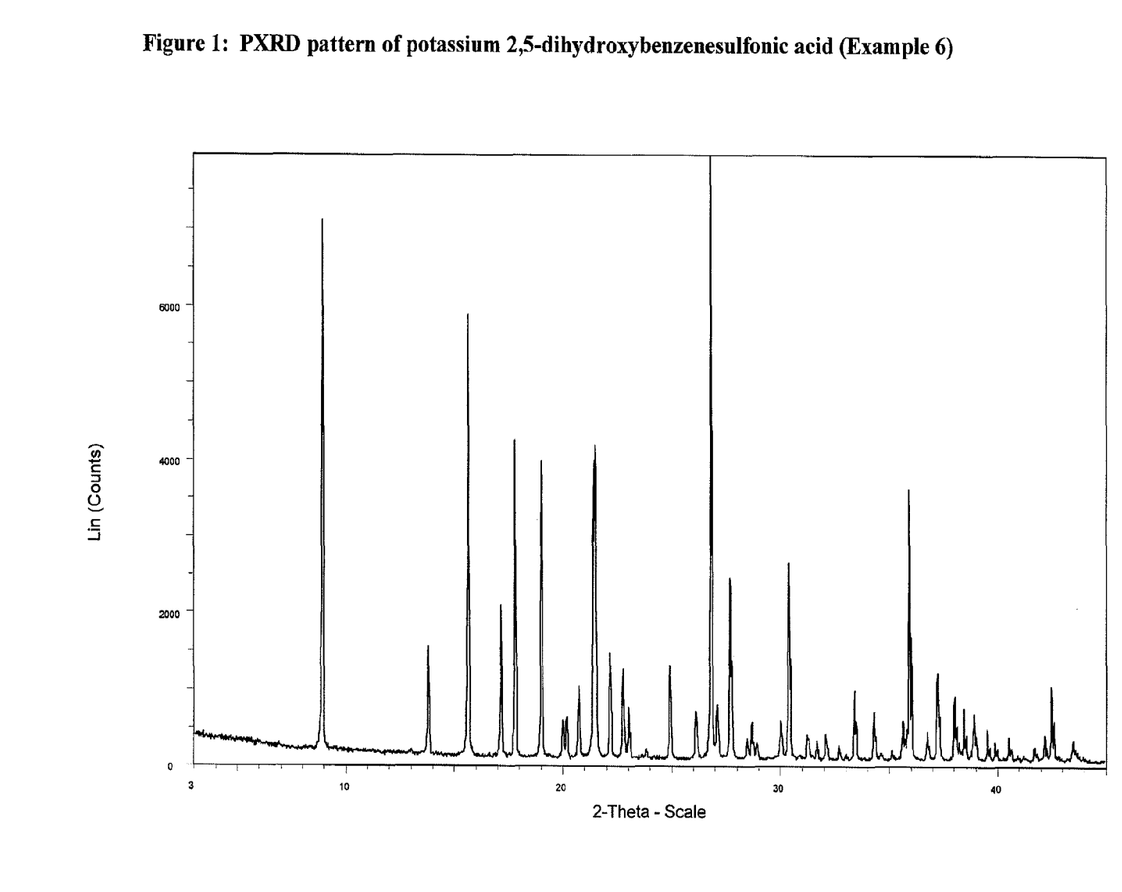
FIG. 1: PXRD pattern of potassium 2,5-dihydroxybenzenesulfonic acid (Example 6).

Hydroquinone (20 g, 0.186 mol) in n-heptane (100 mL) was taken in a round bottom flask, after cooling the flask to 10-15° C., sulfuric acid (36 N, 17.8 g) was added dropwise at the same temperature and stirring continued further for about 10-15 min. Temperature was slowly raised to 53-58° C. then stirring continued for 10 h. The reaction mass was then cooled to 25-35° C. and ethyl acetate (200 mL) added to dissolve the solid formed. A solution of potassium 2-ethylhexanoate (36.46 g, 0.1996 mol) in ethyl acetate (200 mL) was added slowly. The reaction was further stirred for about an hour. The precipitated crude solid was filtered, washed with ethyl acetate. The crude solid obtained was then slurry washed with ethyl acetate. The crude product was dissolved in 2.5 V of dimethylacetamide and 0.5 V methyl isobutyl ketone, filtered and was added 10-15 V of acetonitrile to the filterate to precipitate the product. After stirring for 15 min., the product was filtered, washed with acetonitrile. The product obtained was dissolved in water (3 V) and isopropyl alcohol (5 V) was added. The reaction mixture was filtered; followed by the addition of further 5 V of isopropyl to alcohol. The reaction mass was evaporated under reduced pressure and the total volume was reduced to 1 V. To the reaction mixture was added 15 V of ethyl acetate and then was reduced to 10 V by distilling under reduced pressure to get the pure product. The product was filtered, washed with ethyl acetate and dried. The final product obtained was crystalline in nature and the corresponding PXRD pattern is shown in FIG. 1 and Table A. Yield 18 g.

Table A shows the PXRD values of potassium 2,5-dihydroxybenzenesulfonic acid obtained following Example 6. The corresponding PXRD pattern is given in FIG. 1.

TABLE A

| Angle 2-Theta ° | d value Angstrom | Intensity % |
|---|---|---|
| 8.884 | 9.9453 | 90.0 |
| 12.973 | 6.8188 | 3.0 |
| 13.766 | 6.4278 | 20.1 |
| 15.619 | 5.6689 | 76.6 |
| 17.129 | 5.1724 | 27.1 |
| 17.784 | 4.9835 | 50.3 |
| 18.997 | 4.6680 | 49.2 |
| 19.983 | 4.4398 | 7.7 |
| 20.166 | 4.3998 | 8.4 |
| 20.719 | 4.2837 | 13.7 |
| 21.400 | 4.1488 | 51.3 |
| 21.474 | 4.1346 | 58.2 |
| 22.149 | 4.0103 | 18.9 |
| 22.733 | 3.9085 | 15.7 |
| 22.814 | 3.8948 | 10.8 |
| 23.009 | 3.8621 | 9.4 |
| 23.816 | 3.7331 | 2.9 |
| 24.910 | 3.5716 | 17.5 |
| 26.099 | 3.4116 | 9.4 |

TABLE A-continued

| Angle 2-Theta ° | d value Angstrom | Intensity % |
|---|---|---|
| 26.794 | 3.3246 | 100.0 |
| 26.875 | 3.3148 | 52.7 |
| 27.081 | 3.2900 | 10.9 |
| 27.693 | 3.2187 | 32.5 |
| 28.470 | 3.1326 | 4.6 |
| 28.686 | 3.1095 | 7.3 |
| 28.896 | 3.0874 | 4.1 |
| 30.016 | 2.9747 | 7.9 |
| 30.374 | 2.9404 | 33.8 |
| 30.457 | 2.9326 | 17.7 |
| 31.233 | 2.8614 | 5.3 |
| 31.669 | 2.8230 | 4.0 |
| 32.094 | 2.7867 | 5.8 |
| 32.702 | 2.7362 | 3.5 |
| 33.415 | 2.6794 | 13.2 |
| 33.519 | 2.6714 | 7.5 |
| 34.317 | 2.6110 | 9.3 |
| 34.414 | 2.6039 | 5.5 |
| 34.653 | 2.5865 | 2.6 |
| 35.139 | 2.5518 | 2.6 |
| 35.681 | 2.5143 | 7.6 |
| 35.868 | 2.5016 | 6.3 |
| 35.956 | 2.4957 | 41.8 |
| 36.042 | 2.4900 | 21.4 |
| 36.797 | 2.4406 | 6.0 |
| 36.895 | 2.4343 | 3.4 |
| 37.261 | 2.4112 | 16.7 |
| 37.350 | 2.4057 | 8.8 |
| 38.050 | 2.3630 | 12.4 |
| 38.148 | 2.3572 | 7.0 |
| 38.264 | 2.3503 | 3.9 |
| 38.494 | 2.3368 | 9.7 |
| 38.605 | 2.3303 | 5.3 |
| 38.964 | 2.3097 | 9.1 |
| 39.080 | 2.3031 | 5.3 |
| 39.578 | 2.2753 | 5.7 |
| 39.683 | 2.2694 | 3.4 |
| 39.914 | 2.2569 | 4.1 |
| 40.023 | 2.2510 | 2.8 |
| 40.563 | 2.2222 | 5.0 |
| 40.679 | 2.2162 | 3.1 |
| 41.254 | 2.1866 | 2.0 |
| 41.755 | 2.1615 | 3.2 |
| 41.853 | 2.1567 | 2.2 |
| 42.215 | 2.1390 | 5.2 |
| 42.319 | 2.1340 | 3.2 |
| 42.535 | 2.1236 | 13.5 |
| 42.645 | 2.1185 | 7.6 |
| 43.529 | 2.0774 | 4.6 |
| 43.655 | 2.0717 | 3.2 |

Purification of Potassium Salt of 2,5-dihydroxybenzenesulfonic Acid

Example 7

Crude 2,5-dihydroxybenzenesulfonic acid potassium salt (50 g) was added in water (150 mL) at 25-30° C. and acetone (500 mL), then stirred for 15-30 min. and filtered. The filtrate was concentrated to 50-75 mL. The excess water present in the reaction mixture was again removed by adding 2×250 mL of isopropyl alcohol and distilled upto 50-75 mL under vacuum. To the residue was added 750 mL of ethyl acetate and distilled up to 250-300 mL and the solid formed was filtered and dried to give 25 g of product with assay greater than 98%.

Figure 2:
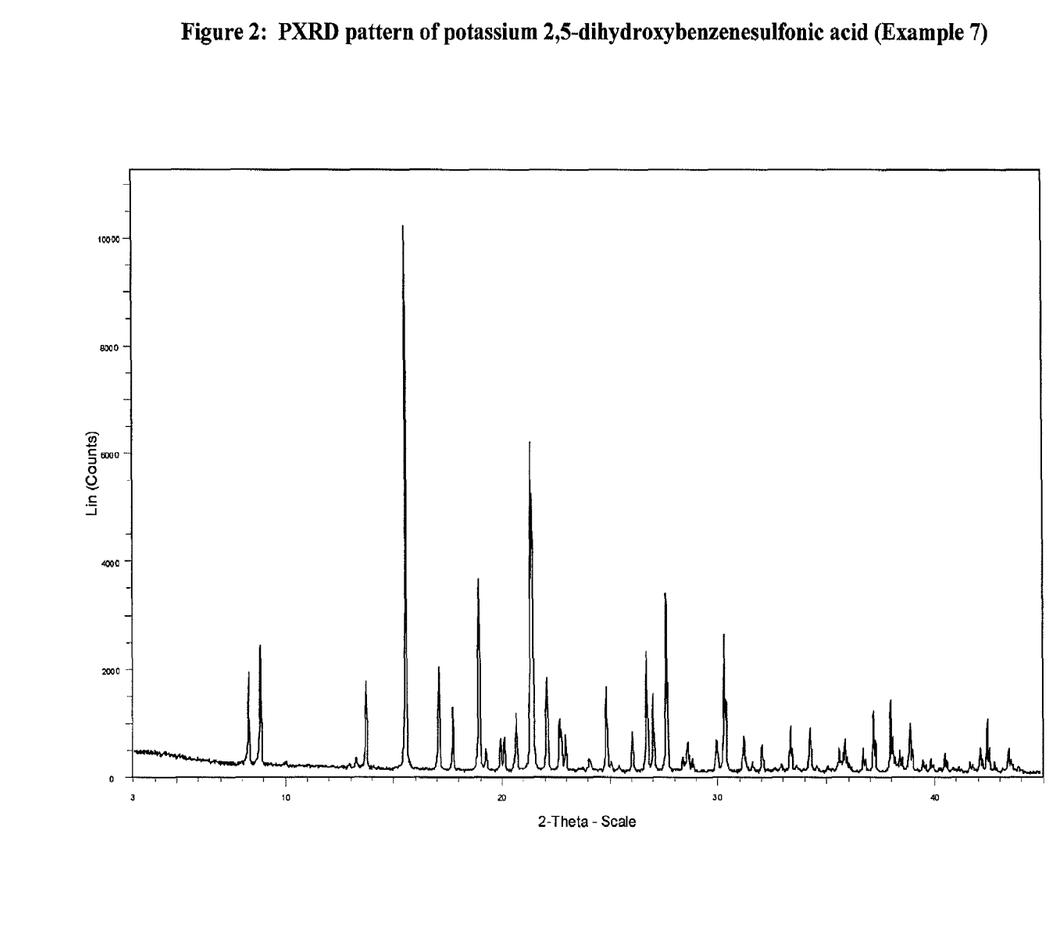
FIG. 2: PXRD pattern of potassium 2,5-dihydroxybenzenesulfonic acid (Example 7)

The compound of formula (I) obtained is crystalline in nature as revealed from the Powder X-ray diffraction (PXRD) data. Table B shows the PXRD values of potassium 2,5-dihydroxybenzenesulfonic acid obtained following Example 7. The corresponding PXRD pattern is shown in FIG. 2.

TABLE B

| Angle 2-Theta | d value Angstrom | Intensity % |
|---|---|---|
| 8.294 | 10.6515 | 20.7 |
| 8.840 | 9.9950 | 25.4 |
| 12.940 | 6.8361 | 2.5 |
| 13.250 | 6.6765 | 3.9 |
| 13.717 | 6.4505 | 18.5 |
| 15.573 | 5.6857 | 100.0 |
| 17.078 | 5.1877 | 19.7 |
| 17.732 | 4.9979 | 12.4 |
| 18.940 | 4.6818 | 37.0 |
| 19.279 | 4.6002 | 5.2 |
| 19.935 | 4.4504 | 7.3 |
| 20.125 | 4.4086 | 7.2 |
| 20.676 | 4.2924 | 12.2 |
| 21.344 | 4.1596 | 58.3 |
| 21.422 | 4.1445 | 58.5 |
| 22.103 | 4.0184 | 19.0 |
| 22.691 | 3.9156 | 10.7 |
| 22.756 | 3.9045 | 9.7 |
| 22.969 | 3.8688 | 7.3 |
| 24.054 | 3.6967 | 3.4 |
| 24.873 | 3.5768 | 16.1 |
| 25.074 | 3.5486 | 2.7 |
| 25.454 | 3.4965 | 2.1 |
| 26.076 | 3.4145 | 8.6 |
| 26.741 | 3.3311 | 23.3 |
| 27.028 | 3.2963 | 15.2 |
| 27.648 | 3.2238 | 34.9 |
| 27.711 | 3.2167 | 18.2 |
| 28.419 | 3.1381 | 3.6 |
| 28.631 | 3.1153 | 6.8 |
| 28.847 | 3.0925 | 3.3 |
| 29.975 | 2.9786 | 7.4 |
| 30.340 | 2.9437 | 26.6 |
| 30.407 | 2.9373 | 14.5 |
| 31.263 | 2.8588 | 7.3 |
| 31.637 | 2.8258 | 2.5 |
| 32.067 | 2.7889 | 6.2 |
| 32.962 | 2.7153 | 2.3 |
| 33.371 | 2.6829 | 9.2 |
| 33.484 | 2.6741 | 5.4 |
| 33.646 | 2.6616 | 2.3 |
| 34.285 | 2.6134 | 9.6 |
| 34.372 | 2.6070 | 5.3 |
| 34.588 | 2.5912 | 1.9 |
| 35.108 | 2.5540 | 2.1 |
| 35.622 | 2.5183 | 5.6 |
| 35.710 | 2.5123 | 3.2 |
| 35.812 | 2.5054 | 4.4 |
| 35.902 | 2.4993 | 7.6 |
| 35.985 | 2.4938 | 3.8 |
| 36.099 | 2.4861 | 3.3 |
| 36.743 | 2.4440 | 5.2 |
| 36.850 | 2.4372 | 3.9 |
| 37.204 | 2.4148 | 12.5 |
| 37.320 | 2.4075 | 7.2 |
| 38.005 | 2.3657 | 14.2 |
| 38.113 | 2.3593 | 8.0 |
| 38.225 | 2.3526 | 4.3 |
| 38.447 | 2.3395 | 5.1 |
| 38.555 | 2.3332 | 3.4 |
| 38.918 | 2.3123 | 9.9 |
| 39.018 | 2.3066 | 5.3 |
| 39.530 | 2.2779 | 3.3 |
| 39.636 | 2.2721 | 2.5 |
| 39.892 | 2.2581 | 3.2 |
| 39.990 | 2.2528 | 2.8 |
| 40.532 | 2.2239 | 4.5 |
| 41.152 | 2.1918 | 1.9 |
| 41.696 | 2.1644 | 2.8 |
| 41.810 | 2.1588 | 2.2 |
| 42.176 | 2.1409 | 4.9 |
| 42.288 | 2.1355 | 3.4 |
| 42.475 | 2.1265 | 10.9 |
| 42.597 | 2.1207 | 5.6 |
| 42.814 | 2.1105 | 2.8 |
| 43.479 | 2.0797 | 5.5 |
| 43.663 | 2.0714 | 3.3 |

TABLE B-continued

| Angle 2-Theta | d value Angstrom | Intensity % |
|---|---|---|
| 43.923 | 2.0597 | 2.2 |
| 44.090 | 2.0523 | 1.3 |

Example 8

To crude 2,5-dihydroxybenzenesulfonic acid potassium salt (50 g) was added water (150 mL) at 25-30° C. and isopropyl alcohol (500 mL) and was stirred for 15-30 min. and filtered. The filtrate was concentrated up to 50-75 mL. To the residue was added 750 mL of ethyl acetate and distilled up to 250-300 mL. The solid formed was filtered and dried to give 22 g of product with assay greater than 98%.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A process for the preparation of compounds of formula (I)

wherein X is at least one cation, and m and n are independently 1 or 2, said process comprising:
i) sulfonation of hydroquinone of formula (II) in the presence or absence of solvent, to provide a compound of formula (III);

ii) treating the compound of formula (III) with a salt of an organic acid comprising potassium 2-ethylhexanoate or calcium 2-ethylhexanoate in a suitable solvent; and
iii) precipitating the product of formula (I).

2. The process according to claim 1, wherein: X is potassium; m is 1; and n is 1.

3. The process according to claim 1, wherein the salt of organic acid used is potassium 2-ethylhexanoate.

4. The process according to claim 1, wherein the salt of organic acid used is potassium 2-ethylhexanoate; X is potassium; m is 1; and n is 1.

5. The process according to claim 1, wherein the salt of organic acid used is calcium 2-ethylhexanoate.

6. The process according to claim 1, wherein the salt of organic acid used is calcium 2-ethylhexanoate; X is calcium; m is 1; and n is 2.

7. The process according to claim 1, wherein the sulfonation is carried out using sulfuric acid, fuming sulfuric acid, or a halosufonic acid.

8. The process according to claim 7, wherein the sulfonation is carried out using sulfuric acid.

9. The process according to claim 1, wherein the solvent used in (i) is selected from the group consisting of $C_5$-$C_{12}$ alkanes, $C_5$-$C_{12}$ cycloalkanes, $C_1$-$C_{12}$ haloalkanes and mixtures thereof.

10. The process according to claim 1, wherein the solvent used in (i) is selected from the group consisting of n-heptane, n-hexane, n-octane, dichloromethane and 1,2-dichloroethane.

11. The process according to claim 1, wherein the solvent used in (ii) is selected from the group consisting of $C_5$-$C_{12}$ alkanes, $C_5$-$C_{12}$ cycloalkanes, $C_1$-$C_{12}$ haloalkanes, $C_2$-$C_8$ alkyl acetates, $C_2$-$C_{12}$ alkyl ethers, $C_5$-$C_{10}$ cycloalkyl ethers and mixtures thereof.

12. The process according to claim 1, wherein the solvent used in (ii) is selected from the group consisting of ethyl acetate, n-heptane, and n-butyl acetate.

13. A process for the preparation of a compound of formula (I)

wherein X is potassium, and m and n are each 1, said process comprising:
i) sulfonation of hydroquinone of formula (II) using sulfuric acid to provide a compound of formula (III);

ii) treating the compound of formula (III) with potassium 2-ethylhexanoate; and
iii) precipitating the product of formula (I).

* * * * *